United States Patent
Fahl

(10) Patent No.: US 12,303,644 B2
(45) Date of Patent: May 20, 2025

(54) SPEAKING VALVE

(71) Applicant: ANDREAS FAHL MEDIZINTECH-NIK-VERTRIEB GMBH, Cologne (DE)

(72) Inventor: Andreas Fahl, Cologne (DE)

(73) Assignee: ANDREAS FAHL MEDIZINTECHNIK-VERTRIEB GMBH, Cologne (DE)

( * ) Notice: Subject to any disclaimer, the term of this patent is extended or adjusted under 35 U.S.C. 154(b) by 828 days.

(21) Appl. No.: 17/603,801

(22) PCT Filed: Apr. 5, 2020

(86) PCT No.: PCT/EP2020/062318
§ 371 (c)(1),
(2) Date: Oct. 14, 2021

(87) PCT Pub. No.: WO2020/225212
PCT Pub. Date: Nov. 12, 2020

(65) Prior Publication Data
US 2022/0193355 A1    Jun. 23, 2022

(30) Foreign Application Priority Data

May 6, 2019    (DE) .......................... 102019111596.5

(51) Int. Cl.
*A61M 16/04*    (2006.01)
*A61F 2/20*    (2006.01)

(52) U.S. Cl.
CPC .......... *A61M 16/0468* (2013.01); *A61F 2/20* (2013.01); *A61M 2205/582* (2013.01)

(58) Field of Classification Search
CPC ... B41M 3/16; G09B 21/003; A61M 16/0468; A61F 2/20
See application file for complete search history.

(56) References Cited

U.S. PATENT DOCUMENTS 5,223,315 A * 6/1993 Katsura ................... B29C 49/24
                                                          264/516
5,709,918 A * 1/1998 Kimijima .................. G09F 3/10
                                                          428/323

(Continued)

FOREIGN PATENT DOCUMENTS

DE    102012024817 A1    6/2014

OTHER PUBLICATIONS

Loc-Dots—Keyboard Key Location Dots (www.magnifyingaids.com/Loc-Dots_Clear; available since Jan. 24, 2007) (Year: 2007).*

(Continued)

*Primary Examiner* — Brandy S Lee
*Assistant Examiner* — Nicholas B. Engel
(74) *Attorney, Agent, or Firm* — Dinsmore & Shohl LLP

(57) ABSTRACT

The invention relates to a speaking valve, having at least a housing and an actuation means for actuating the speaking valve, the actuation means having a distal pressure surface that has a first partial surface and a second partial surface, the first partial surface having a first average roughness (Ra1), and the second partial surface having a second average roughness (Ra2), the first average roughness and the second average roughness differing by about at least 0.1 μm.

6 Claims, 1 Drawing Sheet

(56) References Cited

U.S. PATENT DOCUMENTS

| | | | | |
|---|---|---|---|---|
| 5,779,482 | A * | 7/1998 | Fukumoto | G09B 21/02 206/459.5 |
| 6,090,483 | A * | 7/2000 | Kume | B41M 5/44 428/354 |
| 6,422,235 | B1 * | 7/2002 | Persson | A61F 2/20 128/200.26 |
| 6,596,384 | B1 * | 7/2003 | Day | H05K 3/382 428/209 |
| 7,459,193 | B2 * | 12/2008 | Utz | G09F 3/10 428/40.1 |
| 7,695,584 | B2 * | 4/2010 | Utz | G09F 3/10 156/248 |
| 7,980,711 | B2 * | 7/2011 | Takayanagi | G02B 5/0833 359/267 |
| RE43,261 | E * | 3/2012 | Utz | G09F 3/10 156/248 |
| RE43,275 | E * | 3/2012 | Utz | G09F 3/10 428/40.1 |
| 8,991,394 | B2 * | 3/2015 | Persson | A61F 2/20 128/205.27 |
| 9,259,953 | B2 * | 2/2016 | Tyagi | G03G 15/224 |
| 9,378,665 | B2 * | 6/2016 | Baklanov | G09F 3/02 |
| 9,388,325 | B2 * | 7/2016 | Jones | B65D 83/752 |
| 9,616,699 | B2 * | 4/2017 | Garnier | B42D 25/369 |
| 9,625,065 | B2 * | 4/2017 | Feldhahn | A61M 16/0858 |
| 9,902,878 | B2 * | 2/2018 | Yamamoto | C09J 133/20 |
| 10,034,992 | B2 * | 7/2018 | Schnell | A61M 16/0468 |
| 10,188,817 | B2 | 1/2019 | Fahl | |
| 10,596,792 | B2 * | 3/2020 | Yamamoto | B32B 29/005 |
| 11,104,826 | B2 * | 8/2021 | Yamamoto | C09J 7/203 |
| 11,148,393 | B2 * | 10/2021 | Sugamata | B32B 27/306 |
| 11,691,912 | B2 * | 7/2023 | Tatebe | H01M 50/1245 65/30.14 |
| 11,878,121 | B2 * | 1/2024 | Fahl | A61M 16/201 |
| 2002/0156527 | A1 * | 10/2002 | Persson | A61F 2/20 623/9 |
| 2004/0007313 | A1 * | 1/2004 | Day | H05K 3/382 430/313 |
| 2004/0089291 | A1 * | 5/2004 | Persson | A61M 16/0468 128/200.16 |
| 2005/0270963 | A1 * | 12/2005 | Mishima | G11B 7/24094 369/283 |
| 2006/0141196 | A1 * | 6/2006 | Utz | G09F 3/10 428/40.1 |
| 2008/0032119 | A1 * | 2/2008 | Feldhahn | A61M 16/0825 428/332 |
| 2008/0145532 | A1 * | 6/2008 | McDonald | B29C 44/3484 427/244 |
| 2009/0031841 | A1 * | 2/2009 | Tetsuka | B62M 25/04 74/473.12 |
| 2009/0130363 | A1 * | 5/2009 | Utz | G09F 3/10 156/717 |
| 2009/0244740 | A1 * | 10/2009 | Takayanagi | G02B 5/0833 359/838 |
| 2009/0297820 | A1 * | 12/2009 | Kovalchuk | B29C 55/023 264/173.15 |
| 2010/0279078 | A1 * | 11/2010 | Pan | G03F 7/0752 216/24 |
| 2011/0049865 | A1 * | 3/2011 | Bray | B42D 25/415 283/114 |
| 2011/0220108 | A1 * | 9/2011 | Persson | A61F 2/20 128/205.29 |
| 2013/0059119 | A1 * | 3/2013 | Campeau | B32B 27/32 428/141 |
| 2013/0192602 | A1 * | 8/2013 | Leibitzki | A61M 16/047 128/205.27 |
| 2014/0027064 | A1 * | 1/2014 | Tani | G09F 3/10 156/499 |
| 2014/0150779 | A1 * | 6/2014 | Persson | A61M 16/1055 128/201.13 |
| 2014/0182770 | A1 * | 7/2014 | Baklanov | G09F 3/10 156/60 |
| 2014/0230998 | A1 * | 8/2014 | Tani | B32B 38/145 156/235 |
| 2014/0231006 | A1 * | 8/2014 | Tani | G09F 3/10 156/289 |
| 2015/0093149 | A1 * | 4/2015 | Tyagi | G03G 15/224 399/130 |
| 2015/0238718 | A1 * | 8/2015 | Schnell | A61F 2/20 128/205.27 |
| 2015/0273168 | A1 * | 10/2015 | Fahl | A61M 16/047 128/205.27 |
| 2017/0044404 | A1 * | 2/2017 | Yamamoto | C09J 133/10 |
| 2017/0362461 | A1 * | 12/2017 | Swaans | C08G 18/325 |
| 2019/0344535 | A1 * | 11/2019 | Sugamata | B32B 27/306 |
| 2020/0189973 | A1 * | 6/2020 | Tatebe | C03C 3/083 |

OTHER PUBLICATIONS

International Search Report and Written opinion dated Aug. 7, 2020 pertaining to PCT Application No. PCT/EP2020/062318 filed May 4, 2020.

German Search Report dated Mar. 13, 2020 pertaining to DE102019111596.5 filed May 5, 2019.

* cited by examiner

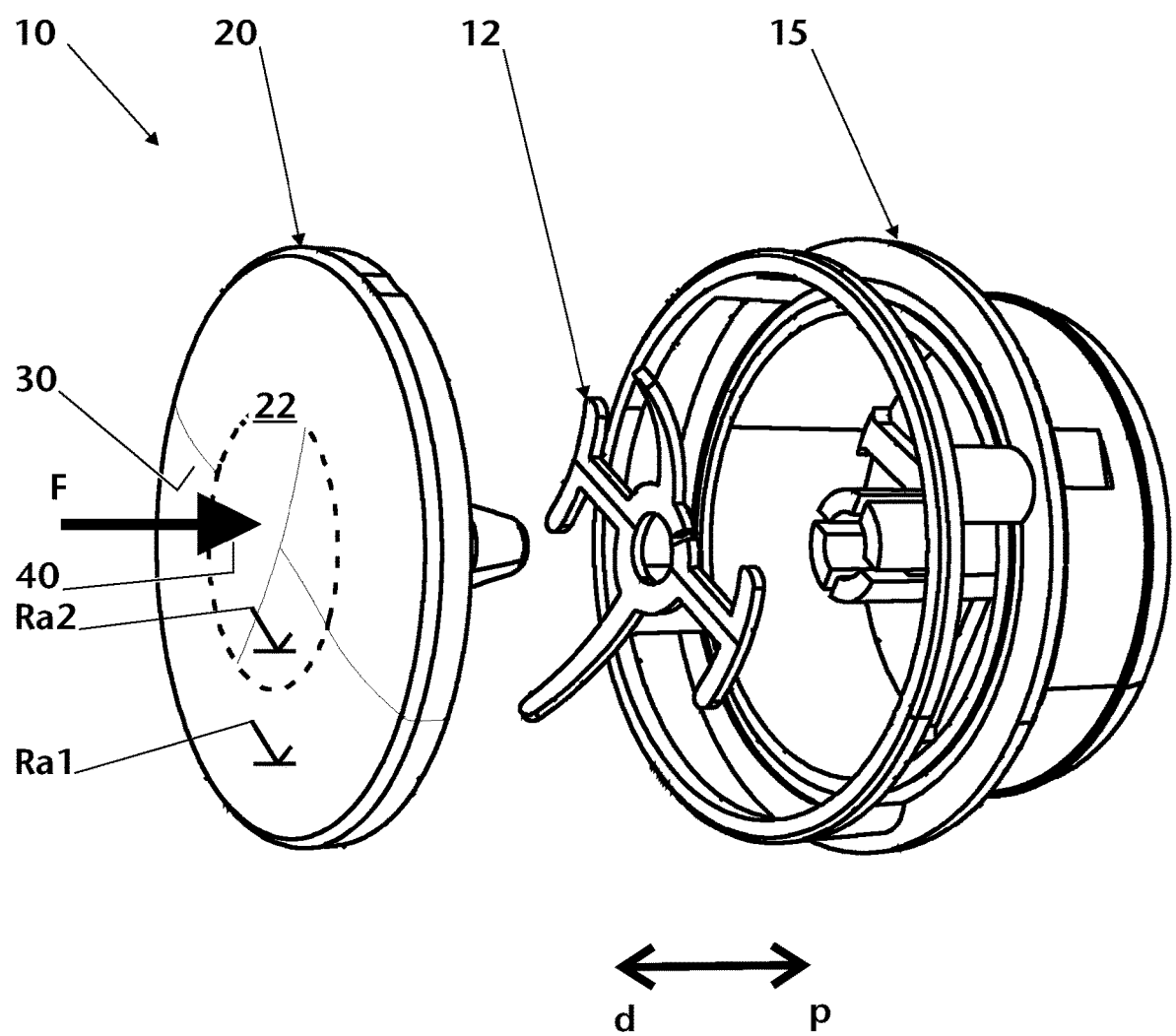

SPEAKING VALVE

CROSS-REFERENCE TO RELATED APPLICATIONS

This application is the U.S. national stage of PCT/EP2020/062318 filed May 4, 2020, which claims priority of German Patent Application 10 2019 111 596.5 filed May 6, 2019 of which is hereby incorporated by reference in its entirety.

FIELD OF THE INVENTION

The invention relates to a speaking valve comprising at least a housing and an actuation structure for actuating the speaking valve.

BACKGROUND OF THE INVENTION

Speaking valves are known from the prior art. For example, DE 10 2013 018 423 A1 shows a speaking valve with a convex actuation means.

The disadvantage of the actuating valves known from the prior art is that they cannot be operated with sufficient precision. An off-center application of force, usually via the user's finger, often leads to a tilting of the valve and consequently to an insufficient closure of the valve. In most cases, the user compensates for this by exerting higher pressure, but this is often perceived as uncomfortable. Geometric aids, such as convex areas, negatively affect the appearance of the speaking valve. Speaking valves are also usually perceived as unadorned.

It is therefore the object of the invention to provide a speaking valve which overcomes the disadvantages of the prior art. In particular, it is the object of the invention to provide a speaking valve which enables the user to actuate the actuation structure with precision and which, preferably, complies with aesthetic aspects.

SUMMARY OF THE INVENTION

The object is solved according to the invention by means of a speaking valve comprising at least a housing and an actuation structure for actuating the speaking valve, the actuation structure having a distal pressure surface comprising a first partial surface and a second partial surface, the first partial surface having a first average roughness and the second partial surface having a second average roughness, the first average roughness and the second average roughness differing by at least about 0.1 µm.

Furthermore, the object is solved according to the invention by means of using an actuation structure of a speaking valve having a distal pressure surface comprising a first partial surface and a second partial surface, the first partial surface having a first average roughness and the second partial surface having a second average roughness, the first average roughness and the second average roughness differing by at least about 0.1 µm, for haptic guidance during actuation of the actuation structure.

DESCRIPTION OF THE DRAWINGS

Further advantageous embodiments are shown in the following drawing. However, the embodiments shown there are not to be interpreted in a limiting manner; rather, the features described there can be combined with each other and with the features described above to form further embodiments. Furthermore, it should be noted that the reference signs given in the description of the FIGURES do not limit the scope of protection of the present invention, but merely refer to the examples of embodiments shown in the figures. It shows FIG. 1, a speaking valve in an explosion view.

DETAILED DESCRIPTION OF THE INVENTION

A speaking valve comprising at least a housing and an actuation structure for actuating the speaking valve is proposed, the actuation structure having a distal pressure surface comprising a first partial surface and a second partial surface, the first partial surface having a first average roughness and the second partial surface having a second average roughness, the first average roughness and the second average roughness differing by at least about 0.1 µm.

If, in the context of the invention, the term "about" is used in connection with values or ranges of values, it is to be understood to mean a range of tolerance which the person skilled in the art considers to be usual in this field, in particular a range of tolerance of 20%, preferably ±10%, more preferably +7%, more preferably +6%, more preferably +5%, more preferably +4% is provided.

In the case of surgical interventions in the upper respiratory tract, it may be necessary to create an artificial breathing opening (tracheostoma) in the trachea so that air can be breathed directly into the lungs, bypassing the oral cavity and larynx. For example, in the case of laryngectomized persons, i.e. persons without a larynx, whose larynx has been surgically removed, the tracheostoma must be kept permanently open and stabilized, for which purpose tracheal cannulae in particular, usually consisting of an outer and an inner cannula, are inserted into the tracheostoma. But the use of so-called "tracheostoma buttons" is also possible, especially for people who no longer need a tracheostomy tube.

Furthermore, so-called "shunt valves" can also be inserted into the tracheostoma, which allow the voice to be restored. Finally, filter systems can also be inserted into the tracheostoma for both tracheostomized and laryngectomized patients. Such filter systems consist in particular of a patch with an inserted filter in a housing or of a usually self-adhesive base plate generally made of plastic, into which filters can be inserted in a housing of various types.

Filter systems used for laryngo-tracheal aids such as tracheal cannulas, shunt valves, tracheostomy buttons and filter systems with patch or base plate include the generic heat and moisture exchangers, also called "artificial nose". These serve to simulate the regulatory mechanisms for heating and humidifying the air breathed by laryngectomized and tracheostomized persons and to prevent the trachea from coming into contact with increasingly dry, cold and unfiltered air. This is because the irritation caused by this leads to increased mucus production with the subsequent risk of clogging. Heat and moisture exchangers moisten, heat and simultaneously filter the inhaled air. This largely prevents the aforementioned formation of clogs. Regular wearing of the artificial nose is particularly helpful in cases of heavy secretion, since moistening of the mucous membranes in the trachea reduces secretion production.

Heat and moisture exchangers for laryngectomized and tracheostomized patients have a filter material—usually made of paper or plastic foam—through which the inhaled and exhaled air is passed. During exhalation, the filter material retains moisture, which is then transported into the trachea during inhalation. Heat and moisture exchangers known from the prior art are available in a large number of different designs for different adapters. A universal adapter according to DIN EN ISO 5356-1 has a diameter of about 15 mm, but other adapters with a diameter of about 22 mm are also known from the prior art.

Another aid for laryngectomized patients are voice prostheses, which are used to restore the voice after a laryngectomy. The voice can be restored by surgical means. The most important aid is a voice prosthesis, also known as a "shunt valve". By means of the voice prosthesis, functions of the removed larynx can be replaced. On the one hand, the use of the voice prosthesis enables an air supply from the lungs via the esophagus into the pharynx. The exhaled air is thereby used for speaking. On the other hand, the voice prosthesis seals the connection from the esophagus to the trachea when swallowing food and drinks, protecting the user of the voice prosthesis from accidentally swallowing food.

Once the wounds have healed after the surgical procedure, people are unable to speak in their normal state. To enable speaking, when using a voice prosthesis or the larynx still in place in tracheotomized people, the air outlet at the neck must be closed so that the air can pass through the voice prosthesis or the larynx, respectively. Speaking valves are used for this purpose.

The speaking valve may, for example, have a valve plate as actuation structure for forming a valve function. In a further embodiment, it is provided that a cover plate, which cooperates with a valve element, for example, serves as an actuation structure. Other embodiments for forming actuation structure are also known from the prior art. Since the components of speaking valves are usually made of thin plastic to save weight, it is important that the actuation structure is operated accurately, otherwise individual parts will be deformed and the speaking valve will not close or not close completely. Also, transverse forces may be felt as uncomfortable on scar tissue surrounding the tracheostoma. Geometric designs of the actuation structure for guidance of the user are known from the prior art, but these have a negative effect on the appearance of the speaking valve.

The advantage of the proposed speaking valve is that the user receives feedback on the basis of different roughness values of the at least two partial surfaces as to where he is located with his finger on the actuation structure. Another advantage is that by providing different roughness values of the at least two partial surfaces, there is no optical separation between the partial surfaces and the pressure surface can be visually perceived as a uniform surface.

The speaking valve comprises the actuation structure, with which a valve function can preferably be actuated indirectly or directly. In one embodiment, the actuation structure comprises at least one material selected from a group comprising plastic and/or metal. Plastics are particularly preferred for the actuation structure. Preferably, the actuation structure is colored. For example, a plastic material of the actuation structure is colored. In one embodiment, a roughness value, in particular the first average roughness or the second average roughness of the pressure surface, can be generated by means of a coloring of the plastic material. In particular, in addition to the selection of the plastic material and the design of the manufacturing tool, the selection of additives, which in particular influence the color of the plastic material, has an influence on a roughness value, in particular the average roughness. In one embodiment, the actuating structure is opaque, translucent or transparent in color. In a further embodiment, the actuation structure is designed in a single color or in multiple colors.

In particular, a marbling with at least two colors can be provided. In a further embodiment, it is provided that additives are added to the plastic material to give a metallic effect. Such actuation structure are, for example, gold-colored, bronze-colored or silver-colored.

The pressure surface is in particular a distal surface of the actuation structure, which is further preferably surrounded by an edge of the housing. In one embodiment, it is provided that the pressure surface is circular. In a further embodiment, the pressure surface is oval or polyhedral in shape, in particular rectangular. In a further embodiment, the pressure surface has a concave and/or convex section. In a further embodiment, it is provided that the first and/or the second partial surface is at least partially convex or concave. In particular, a central surface section of the pressure surface is convex or concave.

In a further preferred embodiment, it is provided that the first partial surface is an edge-side surface portion of the pressure surface. In one embodiment, it is provided that the first partial surface and the second partial surface are concentric to each other. In particular, the first partial surface is a circumferential edge-side surface, further preferably an annular surface, for example a circular ring, an oval ring or a ring adapted to the outer shape of the pressure surface. In particular, the first partial surface surrounds the second partial surface. In a further embodiment, it is provided that the first partial surface is a central surface portion of the pressure surface. In particular, the second partial surface is surrounded by the first partial surface. Preferably, it is provided that the first partial surface is arranged such that an actuating force can be exerted thereon. In particular, the first partial surface is circular, oval or similar in shape to the pressure surface.

In a further embodiment, it is provided that the first partial surface has a first average roughness Ra1. Preferably, the average roughness Ra1 is about 1.4 µm to about 5 µm, preferably about 1.5 µm to about 2 µm. In one embodiment, it is provided that the first partial surface has a first averaged roughness depth Rz1. In particular, the first averaged roughness depth Rz1 is about 7 µm to about 20 µm, preferably about 7 µm to about 15 µm, more preferably about 8 µm to about 11 µm.

In a further embodiment, it is provided that the second partial surface is an actuating surface. Preferably, it is provided that the second partial surface is arranged such that an actuating force can be exerted thereon. In a further embodiment, it is provided that the second partial surface is a central surface portion of the pressure surface. In particular, the second partial surface is surrounded by the first partial surface. In particular, the second partial surface is circular, oval or similar in shape to the pressure surface. In a further embodiment, it is provided that the second partial surface is an edge-side surface portion of the pressure surface. In particular, the second partial surface is a circumferential edge-side surface, further preferably an annular surface, for example a circular ring, an oval ring or a ring adapted to the outer shape of the pressure surface. In particular, the second partial surface surrounds the first partial surface.

In a further embodiment, the second partial surface has a second average roughness Ra2. In particular, the second average roughness Ra2 is about 1.4 µm to about 5 µm, preferably about 1.5 µm to about 2 µm. According to the invention, the first average roughness Ra1 differs from the second average roughness Ra2. Preferably, the value |ΔRa| of the difference between Ra1 and Ra2 is at least about 0.1 µm. More preferably, |ΔRa| is greater than about 0.1 µm, more preferably |ΔRa| is greater than about 0.2 μm, more preferably |ΔRa| is greater than about 0.3 μm, more preferably |ΔRa| is between about 0.1 μm and about 5 μm, more preferably between about 0.1 μm and about 1 μm, further preferred between about 0.1 μm and about 0.5 μm, further preferred between about 0.2 μm and about 0.5 μm, further preferred between about 0.3 μm and 0.5 μm, further preferred between about 0.4 μm and about 0.5 μm.

The neurological and biomechanical processes on which haptic perception is based are extremely complex. Fine surface textures, such as a roughness, cannot be perceived by touch with static pressure of the fingertips, but only by means of dynamic examination, whereby the fingertips sweep over a surface and the skin of the fingertips is mechanically deformed in different ways over time. These dynamic skin deformations are converted into transient signals by the nerve cells embedded in the epidermis and dermis and responsive to mechanical impact, and are transmitted to the central nervous system where they are analyzed. Based on the analysis of the transient signals, the surface texture is classified by the central nervous system. The fingers can perceive very fine structures and can even distinguish different roughnesses of less than about 0.1 μm from each other. The present invention therefore has the advantage that the pressure surface can be divided into haptically different partial areas and the user is optimally guided to press the partial area that results in optimal closure of the speaking valve and is at the same time perceived as comfortable.

In a further embodiment, the second partial surface has a second average roughness depth Rz2. Preferably, the second average roughness depth Rz2 is about 7 μm to about 20 μm, more preferably about 7 μm to about 15 μm, more preferably about 8 μm to about 11 μm.

In one embodiment it is provided that the first partial surface has a first averaged roughness depth Rz1 and the second partial surface has a second averaged roughness depth Rz2, wherein the first averaged roughness depth Rz1 and the second averaged roughness depth Rz2 differ by at least about 0.3 μm. In one embodiment, the first averaged roughness depth Rz1 differs from the second averaged roughness depth Rz2. Preferably, both the average roughness Ra1 and Ra2 and the averaged roughness depths Rz1 and Rz2 differ from each other. Preferably, the value |ΔRz| of the difference between Rz1 and Rz2 is at least about 0.3 μm. In a further embodiment, it is provided that |ΔRz| is greater than about 0.3 μm, more preferably |ΔRz| is greater than about 0.4 μm, more preferably |ΔRz| is greater than about 0.5 μm, more preferably |ΔRz| is between about 0.4 μm and about 10 μm, more preferably between about 0.4 μm and about 5 μm, more preferably between about 0.4 μm and about 3 μm, more preferably between about 0.5 μm and about 0.3 μm.

In one embodiment, it is provided that the first partial surface and/or the second partial surface comprises a varnish, for example a haptic varnish, a sticker, for example a printed sticker, or a surface material that is different from the respective other partial surface. If, for example, a small difference in the roughness values |ΔRa| and/or |ΔRz| is selected, for example |ΔRa| up to about 0.4 μm and/or |ΔRz| up to about 2.5 μm, no or hardly any optical difference is perceived, in particular with regard to a mattness of the surface. The actuating surface appears uniform and is divided into partial surfaces only by haptic differences. In one embodiment, the first partial surface and the second partial surface can differ visually, for example by in particular additionally applying a logo or a pattern to the first partial surface or the second partial surface.

Preferably, a roughness measurement is performed according to DIN EN ISO 4287 (2010-07) or DIN EN ISO 4288 (1998-04)/SOP 4-Scan Section 1 Rev. 4, respectively, to obtain the values mentioned in the scope of the invention. In particular, the following parameters are used for the measurement:
  Measuring device: MarSurf XCR20
  Measuring software: MarWin 9.00-23
  Measuring scanner: BFW A 10-45-2/90°
  Feed unit: MarSurf GD26
  Measuring range: ±250 μm
  Scanning distance: 5.6 mm
  Total measuring distance: 4.0 mm
  Wave filter: 0.8 mm
  Scan tip radius: 2 μm
  Scanning force: 0.7 mN
  Operating mode: free scanning
  No. single measurements: 5/sample It is also preferable to measure a randomly selected segment per sample over an angular range of about 50° to about 60° with 5 individual measurements. In particular, for samples with a sticker, the measurement is performed completely on the sticker. Further preferred optically conspicuous areas as well as areas for example of partial detachment of the sticker are excluded from the measurement zones. Preferably, the distance between 2 individual measurements is between about 10° and about 15° in each case. Preferably, the scanning direction of the individual measurements, relative to the sample surface, runs from the inside to the outside.

In a first exemplary embodiment, it is provided that a first partial surface of a pressure surface is a plastic surface with a metallic color. Furthermore, an exemplary second partial surface is covered with a sticker, which exemplarily has an ornament printed thereon. In the first exemplary embodiment, the partial surfaces have a difference in average roughness |ΔRa| of about 0.4 μm. Furthermore, the partial surfaces have a difference in average roughness depth |ΔRz| of about 5.6 μm. Using the above-mentioned method according to DIN EN ISO 4287, it can further be determined that there is a difference in the averaged largest profile peak |ΔRp| of the partial surfaces of about 1.9 μm. Furthermore, a difference of the averaged depth of the largest profile valley |ΔRv| is about 0.6 μm.

In a second exemplary embodiment, a first partial surface of a pressure surface is a plastic surface having an opaque turquoise color. Further, an exemplary second partial surface is covered with a sticker having an exemplary flower printed thereon. In the second exemplary embodiment, the partial surfaces have a difference in average roughness |ΔRa| of about 0.3 μm. Furthermore, the partial surfaces have a difference in average roughness depth |ΔRz| of about 0.3 μm. Using the above-mentioned method according to DIN EN ISO 4287, it can further be determined that there is a difference in the averaged largest profile peak |ΔRp| of the partial surfaces of about 1.4 μm. Furthermore, a difference of the averaged depth of the largest profile valley |ΔRv| is about 1.2 μm.

An exemplary table of measurement results of a measurement according to DIN EN ISO 4287 with the parameters listed above, in particular averaged after five measurement passes at different locations of the pressure surface or the respective measured partial surface is shown below:

| | $R_a$ [μm] | ± [μm] | $R_z$ [μm] | ± [μm] | $R_p$ [μm] | ± [μm] | $R_v$ [μm] | ± [μm] |
|---|---|---|---|---|---|---|---|---|
| first partial surface (plastic metallic) | 1,811 | 0,060 | 10,016 | 0,475 | 5,557 | 0,403 | 4,459 | 0,138 |
| first partial surface (plastic turquoise color) | 1,546 | 0,060 | 9,198 | 0,446 | 4,224 | 0,144 | 4,974 | 0,508 |
| second partial surface (ornament) | 1,635 | 0,142 | 8,737 | 0,559 | 3,614 | 0,402 | 5,123 | 0,439 |
| second partial surface (flower) | 1,833 | 0,055 | 9,458 | 0,312 | 5,636 | 0,336 | 3,822 | 0,250 |

In one embodiment, the housing comprises a first material and the actuation structure comprises a second material. In one embodiment, the housing comprises at least one housing material selected from a group comprising plastic or metal. Plastics are particularly preferred for the housing. Preferably, the housing is colored. For example, a plastic material of the housing is colored. In one embodiment, the housing is of opaque, translucent or transparent color. In a further embodiment, the housing is designed in one or more colors. In particular, a marbling with at least two colors can be provided. In a further embodiment, it is provided that additives are added to the plastic material of the housing to give a metallic effect. Such housings are, for example, gold-colored, bronze-colored or silver-colored. In one embodiment, the material and/or the colors of the housing and the actuation structure differ. In another embodiment, the housing and actuating structure have substantially the same color. By using different combinations of colors or materials, speaking valves can advantageously be made visually appealing.

The term "substantially" indicates a range of tolerance which is justifiable for the person skilled in the art from an economic and technical point of view, so that the corresponding feature can still be recognized or realized as such.

Further proposed is a use of an actuation structure of a speaking valve comprising at least a housing and an actuation structure for actuating the speaking valve, the actuation structure having a distal pressure surface comprising a first partial surface and a second partial surface, the first partial surface having a first average roughness and the second partial surface having a second average roughness, wherein the first average roughness and the second average roughness differ by at least about 0.1 μm, for haptic guidance upon actuating the actuation structure.

FIG. 1 shows a speaking valve 10 in an explosion view. A housing 15 and an actuation structure 20 can be seen, between which a resetting structure 12 is arranged. In the assembled state of the speaking valve 10, the actuation structure 20 is moved to proximal p by applying force F onto the actuation structure 20 and closes the housing directly to distal d. Other designs of speaking valves can also be provided, in particular in which a closure of the speaking valve 10 is effected indirectly by means of the actuation structure 20 or in which the housing is closed to proximal p.

The actuation structure 20 has a pressure surface 22 on the distal d side, which is divided into a first partial surface 30 and a second partial surface 40, which are separated by a dashed line in FIG. 1 for clarification. The first partial surface 30 has a first average roughness Ra1. The second partial surface 40 has a second average roughness Ra2. The first partial surface 30 and the second partial surface 40 differ in particular in the average roughnesses Ra1 and Ra2, which have a difference in average roughness of at least 0.1 μm.

Advantageously, a haptic guidance of a user for the correct finger position on the actuation structure 20 can be provided by means of the speaking valve 10 without disturbing a visual impression of the speaking valve.

The invention claimed is:

1. A speaking valve comprising:
at least a housing and an actuation structure for actuating the speaking valve, the actuation structure having a distal pressure surface comprising a first partial surface and a second partial surface, said first partial surface having a first average roughness (Ra1) and said second partial surface having a second average roughness (Ra2), wherein said first average roughness (Ra1) and said second average roughness (Ra2) differ by at least 0.1 μm, the first partial surface and the second partial surface are concentric and coplanar to each other.

2. The speaking valve according to claim 1, wherein the first partial surface has a first average roughness depth (Rz1) and the second partial surface has a second average roughness depth (Rz2), wherein the first average roughness depth (Rz1) and the second average roughness depth (Rz2) differ by at least 0.3 μm.

3. The speaking valve according to claim 2, wherein the first averaged roughness depth Rz1 is between 7 μm to 20 μm and the second average roughness depth Rz2 is between 7 μm to 20 μm.

4. The speaking valve according to claim 1 wherein the first partial surface and/or the second partial surface comprises a varnish or a sticker.

5. The speaking valve according to claim 1 wherein the housing comprises a first material and the actuation structure comprises a second material.

6. The speaking valve according to claim 1, wherein the first partial surface and the second partial surface are contiguous to each other.

* * * * *